(12) United States Patent
Che et al.

(10) Patent No.: US 7,393,985 B2
(45) Date of Patent: Jul. 1, 2008

(54) SUPPORTED RUTHENIUM NANOPARTICLE CATALYST FOR CIS-DIHYDROXYLATION AND OXIDATIVE CLEAVAGE OF ALKENES

(75) Inventors: Chi-Ming Che, Hong Kong (HK); Wing-Yiu Yu, Quarry Bay (HK); Chi-Ming Ho, Tin Shui Wai (HK)

(73) Assignee: The University of Hong Kong, Hong Kong (CN)

( * ) Notice: Subject to any disclaimer, the term of this patent is extended or adjusted under 35 U.S.C. 154(b) by 647 days.

(21) Appl. No.: 11/110,317

(22) Filed: Apr. 19, 2005

(65) Prior Publication Data

US 2005/0234260 A1    Oct. 20, 2005

Related U.S. Application Data

(60) Provisional application No. 60/563,645, filed on Apr. 20, 2004.

(51) Int. Cl.
*C07C 29/04* (2006.01)
*C07C 29/03* (2006.01)
(52) U.S. Cl. ............................... 568/860; 568/811
(58) Field of Classification Search ............... 568/860, 568/811
See application file for complete search history.

(56) References Cited

U.S. PATENT DOCUMENTS 2,769,824 A    11/1956    Schneider et al.
6,551,960 B1    4/2003    Laine et al.

OTHER PUBLICATIONS

Haines, A., "Addition Reactions with Formation of Carbon-Oxygen Bonds: (iii) Glycol Forming Reactions," Oxydation C=C Bonds, 437-448, Ch. 3.3 , 1995.
Ojima, I. ed., Catalytic Asymmetric Synthesis, 2000, Wiley-VCH, New York.
Kolb, H.C. et al., "Catalytic Asymmetric Dihydroxylation," Chem. Rev., 1994, 2483-2547, vol. 94, No. 8, American Chemical Society.
Schroder, M., "Osmium Tetraoxide Cis Hydroxylation of Unsaturated Substrates," Chem. Rev., 1980, 187-213, vol. 80, No. 2, American Chemical Society.
Milas, Jr., N.A., et al., "A Study of the Hydroxylation of Olefins . . . ," J. Am. Chem. Soc., 1959, 4730-4733, vol. 81.
Sharpless, K.B. et al., "Osmium Catalyzed Vicinal Hydroxylation of Olefins by tert-Butyl Hydroperoxide under Alkaline Conditions," J. Am. Chem. Soc., 1976, 1986-1987.
Carlsen P.H.J. et al., "A Greatly Improved Procedure for Ruthenium Tetraoxide Catalyzed Oxidations of Organic Compounds," J. Org. Chem., 1981, 3936-3938, vol. 46, No. 19.
Webster, F. et al., "Synthesis of Diacides and Keto Acids by Ruthenium Tetraoxide Catalyzed Oxidation of Cyclic Allylic . . . ," J. Org. Chem., 1987, 689-691, vol. 52, No. 4.
Martin, V.S. et al., "Easy and General Method to Synthesize Chiral 2-Hydroxyacid Benzoates," Tetrahedron Letters, 1988, 2701-2702, vol. 29, No. 22.

Caron, M. et al., "Regioselective Azide Opening of 2,3-Epoxy Alcohols by . . . ," J. Org. Chem., 1988, 5187-5189, vol. 53, American Chemical Society.
Vanrheenen.V. et al., "An Improved Catalytic OsO4 Oxidation of Olefins to CIS-1,2-Glycols . . . ," Tetrahedron Letters, 1976, 1973-1976, No. 23.
Bolm, C. and Gerlach, A., "Polymer-Supported Catalytic Asymmetric Sharpless Dihydroxylations of Olefins," Eur. J. Org. Chem., 1998, 21-27.
Minato, M. et al., "Osmium Tetraoxide Catalyzed Vicinal Hydroxylation of Higher Olefins by Using Hexacyanoferrate (III) . . . ," J. Org. Chem., 1990, 766-768, vol. 55, No. 2.
Ogino, Y. et al., "On the Timing of Hydrolysis/Reoxidation in the Osmium-Catalyzed Asymmetric Dihydroxylation . . . ," Tetrahedron Letters, 1991, 3965-3968, vol. 32, No. 32.
Shing, T. et al., "Practical and Rapid Vicinal Hydroxylation of Alkenes by Catalytic Ruthenium Tetraoxide," Angew. Chem. Int. Ed. Engl., 1994, 2312-2313.
Shing, T. and Tam, E., "Solvent Effect on Ruthenium Catalyzed Dihydroxylation," Tetrahedron Letters, 1999, 2179-2180, vol. 40.
Chen, K. et al., "Olefin Cis-Dihydroxylation versus Epoxidation by Non-Heme Iron Catalysts . . . " J. Am. Chem. Soc., 2002, 3026-3035, vol. 124, No. 12.
Costas, M. et al., "Modeling Rieske Dioxygenases: The First Example of Iron-Catalyzed Asymmetric cis-Dihydroxylation . . . ," J. Am. Chem. Soc., 2001, 6722-6723, vol. 123, No. 27.
Chen, K. and Que, Jr., L., "cis-Dihydroxylation of Olefin by a Non-Heme Iron Catalyst: . . . ," Angew. Chem. Int. Ed., 1999, 2227-2229, vol. 38, No. 15.
De Vos, D.E. et al., "Selective Alkene Oxidation with H2O2 and a Heterogenized Mn Catalyst: . . . ,"Angew. Chem. Int. Ed., 1999, vol. 38, No. 7.
Salvadori, P. et al., "Insoluble Polymer-Bound (IPB) Approach to the Catalytic Asymmetric Dihydroxylation of Alkenes," Synlett, 1999, 1181-1190, No. 8.
Gravert, D. and Janda, K., "Organic Synthesis on Soluble Polymer Supports: Liquid-Phase Methodologies," Chem. Rev., 1997, 489-509, vol. 97, No. 2.
Kobayashi, S. et al., "Catalytic Asymmetric Dihydroxylation of Olefins Using a Recoverable and Reusable . . . ," J. Am. Chem. Soc., 1999, vol. 121, No. 48.
Choudary, B. et al., "Catalytic Asymmetric Dihydroxylation of Olefins with New Catalysts: . . . ," J. Am. Chem. Soc., 2001, 9220-9221, vol. 123, No. 37.
Lee, K. et al., "Osmium Replica of Mesoporous Silicate MCM-48: Efficient and Reusable Catalyst for Oxidative . . . ," J. Am. Chem. Soc., 2003, 6844-6845, vol. 125, No. 23.

(Continued)

*Primary Examiner*—Elvis O Price
(74) *Attorney, Agent, or Firm*—Robert D. Katz; Cooper & Dunham LLP (57) ABSTRACT

The present invention relates to the use of nanosized metal particles (e.g., ruthenium) grafted on inert solid support for oxidation of alkenes. The supported metal catalyst can effect cis-dihydroxylation and oxidative cleavage of alkenes to give the respective cis-diols and carbonyl products.

7 Claims, 2 Drawing Sheets

OTHER PUBLICATIONS

Moreno-Manas, M. and Pleixats, R., "Formation of Carbon-Carbon Bonds Under Catalysis by Transition-Metal Nanoparticles," Acc. Chem. Res., 2003, 638-643, vol. 36.

Roucoux, A., et al., "Reduced Transition Metal Colloids: A Novel Family of Reusable Catalysts?" Chem. Rev., 2002, 3757-3778, vol. 102, No. 10.

Horn, D. and Rieger, J., "Organic Nanoparticles in the Aqueous Phase-Theory, Experiment, and Use," Angew. Chem. Int. Ed., 2001, 4330-4361, vol. 40.

Yang, D. and Zhang, C., "Ruthenium-Catalyzed Oxidative Cleavage of Olefins to Aldehydes," J. Org. Chem., 2001, 4814-4818, vol. 66, No. 14.

Sugiyama, S. et al., "Enhancement of the Selectivity to Carbon Monoxide with Feedstream Doping by . . . ," J. Chem Soc. Faraday Trans., 1996, 293-299, vol. 92, No. 2.

Abstract—Pelzer, K. et al., "Ruthenium Nanoparticles in Nanoporous Alumina Membranes: . . . ," Zeitschrift Fur Anorganische Und Allegemeine Chemie, 2003, 1217-1222.

Plietker, B. and Niggemann, M., "An Improved Protocol for the RuO4-Catalyzed Dihydroxylation of Olefins," Org. Ltrs., 2003, 3353-3356, vol. 5, No. 18.

Hayek, E. and Newesely, H., "Pentacalcium Monohydroxyorthophosphate" Inorganic Synthesis, 1963, 63-65, Innsbruck University, Austria.

Bonnemann, H. and Richards, R.M., "Nanoscopic Metal Particles-Synthetic Methods and Potential Applications," Eur. J. Inorg. Chem., 2001, 2455-2480.

Rao, C.N.R., et al., "Metal Nanoparticles and Their Assemblies," Chem. Soc. Chem., 2000, 27-35, vol. 29.

Johnson, B.F.G., "From Clusters to Nanoparticles and Catalysis," Coordination Chemistry Reviews, 1999, 1269-1285, 190-192, Elsevier.

Abstract—Schmid, G., Clusters and Colloids: From Theory to Applications, 1994, Weinheim.

Lewis, L.N., "Chemical Catalysis by Colloids and Clusters," Chem. Rev., 1993, 2693-2730, vol. 93, No. 8, American Chemical Society.

Schmid, G., "Large Clusters and Colloids. Metals in the Embryonic State," Chem. Rev., 1992, 1709-1727, vol. 92, No. 8, American Chemical Society.

Viau, G., et al., "Ruthenium Nanoparticles: Size, Shape, and Self-Assemblies," Chem. Mater, 2003, 486-494, vol. 15, No. 2, American Chemical Society.

Ishiguro, A. et al., "Nanoparticles of Amorphous Ruthenium Sulfide Easily Obtainable a TiO2-Supported Hexanuclear Cluster . . . ," Chem. Eur. J., 2002, 3260-3268, vol. 8, No. 14.

Miyazaki, A. et al., "Preparation of Ru Nanoparticles Supported on y-Al2O3 and Its Novel Catalytic Activity . . . ," Journal of Catalysis, 2001, 364-371, vol. 204.

Vidoni, O. et al., "Novel, Spongelike Ruthenium Particles of Controllable Size Stabilized Only b Organic Solvents," Angew. Chem. Int. Ed., 1999, 3736-3738, vol. 38, No. 24.

Gao, S. et al., "A Convenient Solvothermal Route to Ruthenium Nanoparticles," New J. Chem., 2000, 739-740, vol. 24.

Vogel, W. et al., "Ru Clusters Synthesized Chemically from Dissolved Carbonyl: . . . ," J. Phys. Chem. B, 2001, 5238-5243, vol. 105, No. 22.

Balint, I. et al., "Methane Reaction with No over Alumina-Supported Ru Nanoparticles," Journal of Catalysis, 2002, 66-75, vol. 207.

Zhang, X. and Chan, K-Y., "Water-in-Oil Microemulsion Synthesis of Platinum-Ruthenium Nanoparticles, . . . ," Chem. Mater, 2003, 451-459, vol. 15, No. 2.

Zhan, B. et al., "Zeolite-Confined Nano-RuO2: A Green, Selective, and Efficient Catalyst for Aerobic Alcohol Oxidation," J. Am. Chem. Soc., 2003, 2195-2199, vol. 125, No. 8.

Meunier, B. et al., Biomimetic Oxidations Catalyzed by Transition Metal Complexes, 2000, Imperial College Press, London.

Abstract—Ley, S.V. et al., "Tetrapropylammonium Perruthenate, PR4N+RUO4-, TPAP—A Catalytic Oxidant for Organic-Synthesis," Synthesis-Stuttgart, 1994, 639-666.

Abstract—Elliott, J.C., Structure and Chemistry of the Apatites and Other Calcium Orthophosphates, 1994, Elsevier.

Griffith, W.P., "Ruthenium Oxo Complexes as Organic Oxidants," Chemical Society Reviews, 1992, 179-185, Imperial College of Science, Technology, and Medicine, London.

SUPPORTED RUTHENIUM NANOPARTICLE CATALYST FOR CIS-DIHYDROXYLATION AND OXIDATIVE CLEAVAGE OF ALKENES

This application claims benefit to provisional application No. 60/563,645, filed Apr. 20, 2004.

FIELD OF THE INVENTION

The invention relates to the use of supported ruthenium nanoparticles as a catalyst for oxidation of alkenes, including cis-dihydroxylation and oxidative cleavage of alkenes.

BACKGROUND OF THE INVENTION

Figure 1:
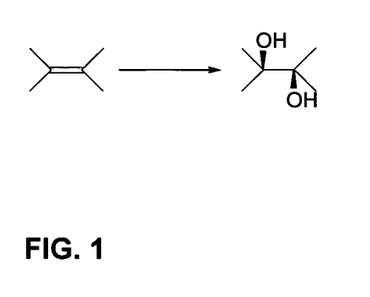
FIG. 1. illustrates the described cis-addition of two hydroxyl group to the carbon-carbon double bond.

The addition of two hydroxy groups in a cis manner to the carbon-carbon double bond of an alkene, as shown in FIG. 1, is an important transformation in organic synthesis. The resulting cis-1,2-diol products are versatile building blocks for pharmaceutical products and fine chemicals.

Traditionally, cis-dihydroxylation can be performed using stoichiometric amounts of osmium tetroxide or potassium permanganate (see: Haines, A. H., in *Comprehensive Organic Synthesis*; Trost, B. M.; Fleming, I. (eds.) Pergamon: Oxford, 1991; Vol. 7, p. 437). However, an immediate drawback is that these processes produce a large amount of toxic effluent. Furthermore, osmium tetroxide is highly toxic and very expensive, which hampers its use in large-scale synthesis. For the use of permanganate as oxidant, the reaction usually produces undesired over-oxidized products, and yields are lower than with osmium tetroxide.

Catalytic systems for alkene cis-dihydroxylation have been extensively pursued. In particular, development of osmium-catalyzed alkene dihydroxylation and its asymmetric variants represents an important milestone in modern organic synthesis [see: (a) Johnson, R. A.; Sharpless, K. B. In *Catalytic Asymmetric Synthesis*; by Ojima, I. 2$^{nd}$ ed., VCH: New York, 2000. (b) Kolb, H. C.; Van Nieuwenhze, M. S.; Sharpless, K. B. *Chem. Rev.* 1994, 94, 2483]. Several secondary oxidants including metal chlorates (see: Hofman, K. A. *ChemBer.* 1912, 45, 3329), hydrogen peroxide (see: Milas, N. A.; Trepagnier, J.-H.; Nolan, J. T.; Iliopolus, J. Ji. *J. Am. Chem. Soc.* 1959, 81, 4730), tert-butyl hydroperoxide [see: (a) Sharpless, K. B.; Akashi, K. *J. Am. Chem. Soc.* 1976, 98, 1986. (b) Carlsen, P. H. J.; Katsuki, T.; Martin, V. S.; Sharpless, K. B. *J. Org. Chem.* 1981, 46, 3936. (c) Webster, F. X.; Rivas-Enterrios, J.; Silverstein, R. M. *J. Org. Chem.* 1987, 52, 689. (d) Martin, V. S.; Nunez, M. T.; Tonn, C. E. *Tetrahedron Lett.* 1988, 29, 2701 (e) Caron, M.; Carlier, P. R.; Sharpless, K. B. *J. Org. Chem.* 1988, 53, 5185], N-methylmorpholine N-oxide (NMO, Upjohn process) [see: (a) Schneider, W. P.; McIntosh, A. V. U.S. Pat. No. 2,769,824 (1956). (b) Van Rheenen, V.; Kelly, R. C.; Cha, D. Y. *Tetrahedron Lett.* 1976, 17, 1973] are known for effective catalytic cis-dihydroxylation reactions. For sterically hindered alkenes, the catalytic system employing trimethylammonia N-oxide as secondary oxidant has been reported to give improved product yields (see: Ray, R.; Matteson, D. S. *Tetrahedron Lett.* 1980, 21, 449).

To overcome problems of over-oxidation and inertness towards sterically hindered alkenes, catalytic system using hexacyanoferrate(III) as secondary oxidant has been developed (see: Minato, M.; Yamamoto, K.; Tsuji, J. *J. Org. Chem.* 1990, 55, 766). Consequently, an enantioselective version based on hexacyanoferrate(III) as oxidant was developed by Sharpless and co-workers (see: Ogino, Y.; Chen, H.; Kwong, H. L.; Sharpless, K. B. *Tetrahedron Lett.* 1991, 32, 3965). Currently, the "K$_2$[OsO$_2$(OH)$_4$+K$_3$[Fe(CN)$_6$]" formulation is commercially available and branded as AD-mix.

The search for transition metal catalysts alternative to osmium for cis-dihydroxylation of alkene is receiving current attention. Earlier work by Shing and co-workers showed that RuCl$_3$·xH$_2$O is an effective catalyst for cis-dihydroxylation of alkenes when using NaIO$_4$ as oxidant with a mixture of acetonitrile, ethyl acetate and water as solvent at reaction temperature=0° C. [see: (a) Shing, T. K. M.; Tai, V. W.-F.; Tam, E. K. M. *Angew. Chem., Int. Ed. Engl.* 1994, 33, 2313. (b) Shing, T. K. M.; Tai, V. W. F.; Tam, E. K. M. Chung, I. H. F.; Jiang, Q. *Chem. Eur. J.* 1996, 2, 50. (c) Shing, T. K. M.; Tam, E. K. M. *Tetrahedron Lett.* 1999, 40, 2179]. Recently, Que and co-workers disclosed that alkene cis-dihydroxylation can be achieved with moderate selectivity using some iron complexes as catalyst and hydrogen peroxide as oxidant [see: (a) Chen, K.; Costas, M.; Kim, J.; Tipton, A. K.; Que, L. Jr. *J. Am. Chem. Soc.* 2002, 124, 3026. (b) Costas, M.; Tipton, A. K.; Chen, K.; Jo, D.-H.; Que, L. Jr. *J. Am. Chem. Soc.* 2001, 123, 6722. (c) Chen, K.; Que, L. Jr. *Angew. Chem. Int Ed.* 1999, 38, 2227]. In addition, Jacobs and coworkers reported that some manganese cyclic triamine complexes could convert alkene to its corresponding cis-1,2-diol in low yield using hydrogen peroxide as secondary oxidant (see: De Vos, D. E.; de Wildeman, S.; Sels, B. F.; Grobet, P. J.; Jacobs, P. A. *Angew. Chem. Int. Ed.* 1999, 38, 980).

At present, osmium-catalyzed alkene cis-dihydroxylation is still the system of choice because of its effectiveness and selectivity. However, recovery of the precious metal catalysts are difficult, and it may result in product contamination. This has restricted its use for large-scale reactions in industry. To this end, several research groups have already attempted to address the issues by heterogenization of the metal catalysts onto solid support[see: (a) Bolm, C.; Gerlach, A. *Chem. Eur. J.* 1998, 1, 21. (b) Salvadori, P.; Pini, D.; Petri, A. *Synlett.* 1999, 1181. (c) Gravert, D. J.; Janda, K. D. *Chem. Rev.* 1997, 97, 489. However, limited success was achieved with respect to recovery and reuse of the metal catalysts. For example, Kobayashi and co-workers recently developed a highly recoverable and reusable polymer-supported osmium catalyst for alkene cis-dihydroxylations using a microencapsulation technique (see: Kobayashi, S.; Endo, M.; Nagayama, S. *J. Am. Chem. Soc.* 1999, 121, 11229). A recent work by Choudary and co-workers reported that immobilized OsO$_4^{2-}$ on layered double hydroxides by ion-exchange technique was found to attain good recoverability and reusability for alkene cis-dihydroxylation (see: Choudary, B, M.; Chowdari, N. S.; Kantam, M. L.; Raghavan, K. V. *J. Am. Chem. Soc.* 2001, 123, 9220). Despite these advances, development of more easily handled metal catalysts with superior recyclability and catalytic activities is still highly desirable. A recent report by Park and co-workers showed that a 3-D networked osmium nanomaterial is an effective heterogeneous catalyst for dihydroxylation and oxidative cleavage of alkenes (see: Lee, K.; Kim, Y.-H.; Han, S. B.; Kang, H.; Park, S.; Seo, W. S.; Park, J. T.; Kim, B.; Chang, S. *J. Am. Chem. Soc.* 2003, 125, 6844).

Limited examples involving supporting transition metal catalysts other than osmium based complexes for alkene cis-dihydroxylation and alkene oxidative cleavage have been reported. Supported manganese cyclic triamine complexes converted alkenes to cis-diols when using hydrogen peroxide as oxidant, but poor yield and selectivity made this process impractical (De Vos, D. E.; de Wildeman, S.; Sels, B. F.; Grobet, P. J.; Jacobs, P. A. *Angew. Chem. Int. Ed.* 1999, 38, 980).

Application of nanosized metal particles as catalysts for organic transformations is receiving current attention [see: (a)

Moreno-Mañas, M.; Pleixats, R. *Acc. Chem. Res.* 2003, 36, 638. (b) Roucoux, A.; Schulz, J.; Patin, H. *Chem. Rev.* 2002, 102, 3757. (c) Horn, D.; Rieger, J. *Angew. Chem. Int. Ed.* 2001, 40, 4330. (d) Bönnermann, H.; Richards, R. M. *Eur. J. Inorg. Chem.* 2001, 2455. (e) Rao, C. N. R.; Kulkarni, G. U.; Thomas, P. J.; Edwards, P. P. *Chem. Soc. Rev.* 2000, 29, 27. (f) Johnson, B. F. G. *Coord. Chem. Rev.* 1999, 190, 1269. (g) Bradley, J. S. In *Clusters and Colloids: from Theory to Application*; Ed.: Schmid, G. VCH: Weiheim, 1994; p. 459. (h) Lewis, L. N. *Chem. Rev.* 1993, 93, 2693. (i) Schmid, G. *Chem. Rev.* 1992, 92, 1709]. Due to its high surface area and the high density of active sites, nanosized metal particles exhibit superior catalytic activities versus the corresponding bulk materials.

Various synthetic methods for ruthenium nanoparticles have been reported in the literature. The reduction of ruthenium salts in polyol solution at evaluated temperature is promising and simple for ruthenium nanoparticles [see: (a) Viau, G.; Brayner, R.; Poul, L.; Chakroune, N.; Lacaze, E.; Fiévet-Vincent, F.; Fiévet, F. *Chem. Mater.* 2003, 15, 486. (b) Balint, I.; Mayzaki, A.; Aika, K.-I. *J. Catal.* 2002, 207, 66. (c) Miyazaki, A.; Balint, I.; Aika, K.-I.; Nakano, Y. *J. Catal.* 2001, 204, 364]. Besides, several research groups have developed some new preparation procedures for nanosized ruthenium particles. Chaudret and co-workers utilized the reaction of an organometallic ruthenium precursor under a hydrogen atmosphere in organic solvent to obtain a stable ruthenium colloid (see: Vidoni, O.; Philipport, K.; Amiens, C.; Chaudret, B.; Balmes, O.; Malm, J. O.; Bovin, J. O. Senocq, F.; Casanove, J. *Angew. Chem. Int. Ed. Engl.* 1999, 38, 3736). Also, Che and coworkers demonstrated that the solvothermal reduction of ruthenium salts is a viable route to nanosized ruthenium particles (see: Gao, S.; Zhang, J.; Zhu, Y.-F.; Che, C. M. *New J. Chem.* 2000, 739). In addition, Alonso-Vante and co-workers disclosed that highly dispersed nanocrystalline ruthenium particles could be prepared under mild conditions in an organic solvent from the ruthenium carbonyl precursor (see: Vogel, W.; Le Rhun, V.; Garnier, E.; Alonso-Vante, N. *J. Phys. Chem. Chem. B* 2001, 105, 5238). Furthermore, Lee and coworkers reported that nanosized ruthenium particles could be prepared by the sodium borohydride reduction of ruthenium chloride and ruthenium hydroxide (see: Lee, D.-S.; Liu, T.-K. *Journal of Non-Crystalline Solids*, 2002, 311, 323).

The reports on the catalytic reactivity of these ruthenium particles are, however, sparse in the literature. Miyazaki and co-workers reported alumina-supported ruthenium nanoparticles have a high reactivity for ammonia synthesis [see: (a) Balint, I.; Mayzaki, A.; Aika, K.-I. *J. Catal.* 2002, 207, 66. (b) Miyazaki, A.; Balint, I.; Aika, K.-I.; Nakano, Y. *J. Catal.* 2001, 204, 364]. Wakatsuki and coworker disclosed that $TiO_2$-supported ruthenium nanosized metal particles exhibited the reduction of $SO_2$ and $H_2$ to give element sulfur (see: Ishiguro, A.; Nakajima, T.; Iwata, T.; Fujita, M.; Minato, T.; Kiyotaki, F.; Izumi, Y.; Aika, K.-I.; Uchida, M.; Kimoto, K.; Matsui, Y.; Wakatsuki, Y. *Chem. Eur. J.* 2002, 8, 3260). Schmid and co-workers revealed that ruthenium nanoparticles included in nanoporous alumina membranes catalyzed alkene hydrogenation (see: Pelzer, K.; Philippot, K.; Chaudret, B.; Meyer-Zaika, W.; Schmid, G. *Zeitschrift fur anorganische und allgemieine chemie*, 2003, 629, 1217). U.S. Pat. No. 6,551,960 discloses the fabrication of supported nanosized ruthenium catalyst and its reactivity for methanol reformation. Chan and co-workers reported that Ru—Pt nanoparticles, prepared by water-in-oil reverse micro-emulsion, displaced high catalytic activity for methanol oxidation when supported on carbon electrode (see: Zhang, Z.; Chan, K.-Y. *Chem. Mater.* 2003, 15, 451). Recently, it was reported that zeolited-confined nanosized ruthenium dioxide can efficiently promote aerobic oxidation of alcohols (see: Zhan, B.-Z.; White, M. A.; Sham, T.-K.; Pincock, J. A.; Doucet, R. J.; Rao, K. V. R.; Roberson, K. N.; Cameron, T. S. *J. Am. Chem. Soc.* 2003, 125, 2195). However, the reactivities of ruthenium nanoparticles toward cis-dihydroxylation and oxidative cleavage of alkenes are hitherto unknown in the literature.

Ruthenium salts and complexes are known to be versatile catalysts for various oxidative transformations [see: (a) Murahashi, S.-I.; Komiya, N. In *Biomimetic Oxidations Catalyzed by Transition Metal Complexes*; Ed.: Meunier, B.; Imperial College Press, 2000; p. 563. (b) McLain, J. L.; Lee, J.; Groves, J. T. In *Biomimetic Oxidations Catalyzed by Transition Metal Complexes*; Ed.: Meunier, B.; Imperial College Press, 2000; p. 91. (c) Ley, S. V.; Norman, J.; Griffith, W. P.; Marsden, S. P. *Synthesis*, 1994, 639. (d) Griffith, W. P. *Chem. Soc. Rev.* 1992, 21, 179]. Here, we report that ruthenium nanoparticles immobilized on hydroxyapatite is a superior catalyst for cis-dihydroxylation and oxidative cleavage of alkenes. With ethyl trans-cinnamate as a substrate, the supported catalyst has been recycled for successive cis-dihydroxylation reactions without significant deterioration of catalytic activities.

BRIEF DESCRIPTION OF THE FIGURES AND TABLES

TABLE 1. provides representative examples of cis-dihydroxylation of alkenes catalyzed by ruthenium nanoparticles.

TABLE 2. provides representative examples of oxidative cleavage of alkenes catalyzed by ruthenium nanoparticles.

TABLE 3. provides representative examples of oxidative cleavage of α,β-unsaturated alkenes catalyzed by ruthenium nanoparticles.

DETAILED DESCRIPTION OF THE INVENTION

The invention relates to the use of ruthenium colloids supported on an inert solid support (e.g., calcium hydroxyapatite) for oxidative transformations of alkenes. Stable ruthenium colloid was prepared by the reduction of $RuCl_3.xH_2O$ (0.32 mmol) in 1,2 immobilization of ruthenium colloids onto calcium hydroxyapatite. Stable ruthenium colloid was prepared by the reduction of $RuCl_3.xH_2O$ (0.325 mmol) in 1,2-propanediol (100 mL) in the presence of sodium acetate (1 mmol) at 150° C. by following a reported procedure (see: Viau, G.; Brayner, R.; Poul, L.; Chakroune, N.; Lacaze, E.; Fiévet-Vincent, F.; Fiévet, F. *Chem. Mater.* 2003, 15, 486).

In this work, we chose calcium hydroxyapatite as an example of solid support. Reported uses of hydroxyapatite include artificial bones and teeth, adsorbents, ion-exchangers, and catalysts [see: (a) Elliott, J. C. *Structure and Chemistry of the Apatite and Other Calcium Orthophosphates*; Elsevier, Amsterdam, 1994. (b) Sugiyama, S.; Minami, T.; Hayashi, H.; Tanaka, M.; Shigemoto, N.; Moffat, J. B. *J. Chem. Soc. Faraday Trans.* 1996, 92, 293]. Calcium hydroxyapatite was prepared according to a reported method (see: Hayek, E.; Newesely, H. *Inorg. Synth.* 1963, 7, 63). Successful immobilization of the ruthenium nanoparticles was achieved by treating the colloidal solution with calcium hydroxylapatite (0.4 g) and $H_2O$ (50 mL) for 24 h. The hydroxyapatite-supported ruthenium nanoparticles (nano-RuHAP) were obtained as a dark grey solid after centrifugation, followed by washing with deionized water and dried under vacuum at 110° C. for overnight. On the basis of ICP analysis, the Ru content of nano-RuHAP was determined to be 5 wt % (0.5 mmol $g^{-1}$) and the measured Ca/P molar ratio being 1.66, which agrees with the reported value of 1.67, indicating no significant exchange of the constituent $Ca^{2+}$ ions.

Figure 2:
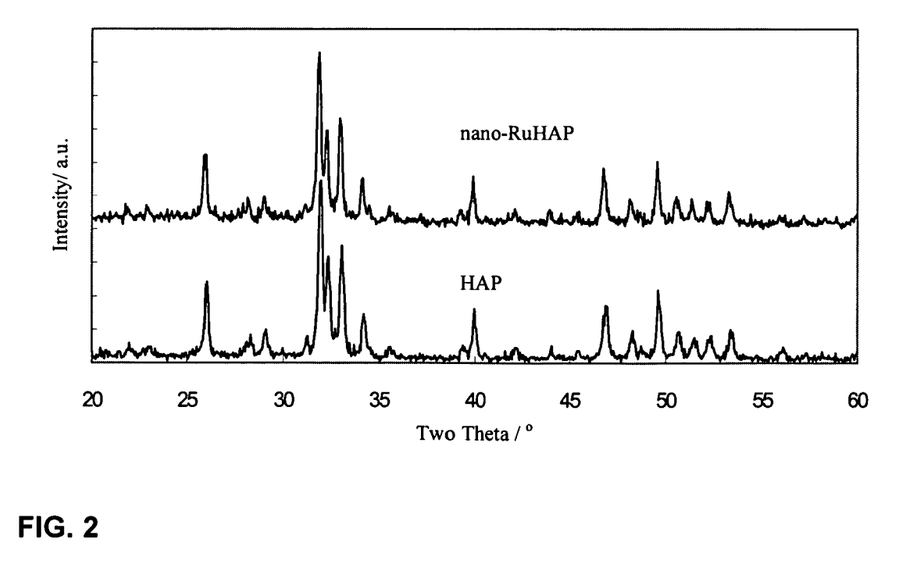
FIG. 2. provides a typical transmission electron micrograph of hydroxyapatite supported ruthenium nanoparticles catalyst.
Figure 3:
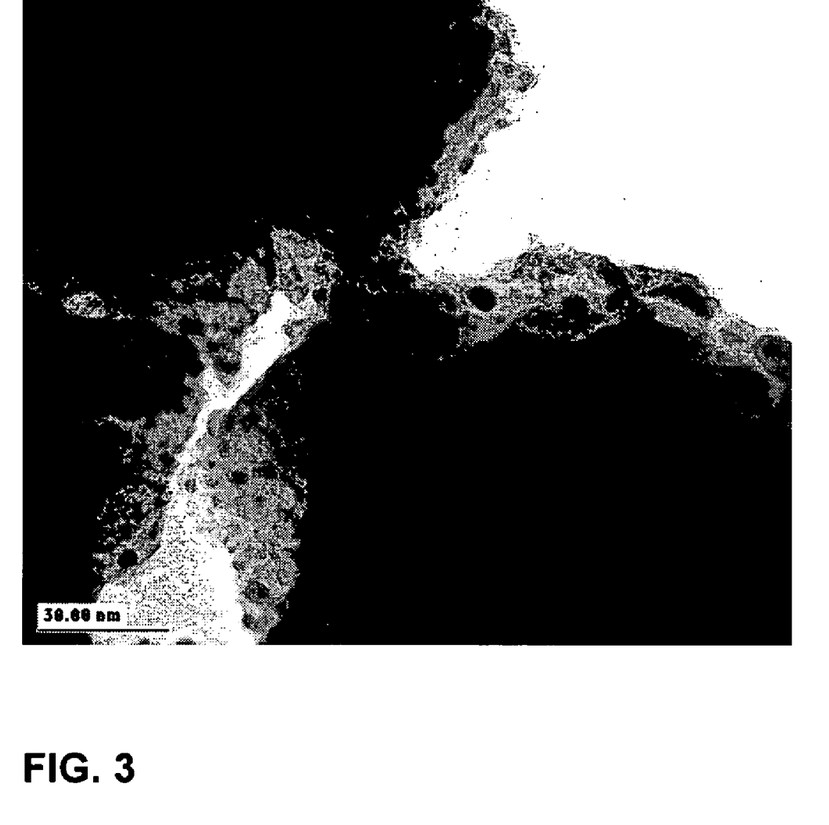
FIG. 3. provides an X-ray diffraction (XRD) spectrum of hydroxyapatite supported ruthenium nanoparticles catalyst and its parent hydroxyapatite as control.

The X-ray powder diffraction (XRD) pattern of nano-RuHAP showed prominent peaks at 2θ=25.90°, 31.85°, 32.25°, 32.95° and 49.55°, which are indexed to (002), (211), (112), (300) and (213) reflections of the hexagonal crystal system of the hydroxyapatite [JCPSD card no: 09-0432], respectively (FIG. 2). It should be noted that almost identical XRD pattern was observed for the free hydroxyapatite (i.e., without Ru particles). This result indicates that the crystallinity of hydroxyapatite was retained after immobilization of ruthenium nanoparticles. The transmission electron microscope (TEM) image of nano-RuHAP showed uniformly dispersed particles, and EDX analysis confirmed that the particles corresponded to ruthenium with an average diameter being ca. 4 nm (FIG. 3). There is a small increase in the surface area of nano-RuHAP (25 $m^2$ $g^{-1}$) compared to its parent hydroxyapatite (17 $m^2$ $g^{-1}$) as determined by the $N_2$ adsorption isotherms. This can be accounted for by the physical adsorption of the ruthenium nanoparticles on the solid support.

EXAMPLE 1 cis-Dihydroxylation of Alkenes Catalyzed by nano-RuHAP

The invention relates to a direct method of synthesis of cis-1,2-diol using nano-RuHAP as a general and effective catalyst for the direct cis-dihydroxylation of alkenes. Generally, to a dilute sulfuric acid solution (0.4 N, 2 mL) was added $NaIO_4$ (642 mg, 3 mmol) with stirring to form a clear solution. Upon cooling to 0° C. using an ice-water bath, nano-RuHAP (40 mg) was added and the mixture was stirred for 3 min, followed by addition of an EtOAc-MeCN mixture (1:1 (v/v); 12 mL). The combined mixture was stirred at 0° C. for an additional 5 min. Alkene (2 mmol) was added in one portion and the reaction mixture was stirred until all the starting alkene was consumed as monitored by TLC. Excess acid and $NaIO_4$ were quenched using a saturated $NaHCO_3$ solution (10 mL) and a saturated $Na_2S_2O_3$ solution (10 mL). The catalyst was separated from the reaction mixture by centrifugation. The recovered catalyst was washed with water and then dried in vacuum before recycle. The supernatant liquid was extracted with ethyl acetate (3×15 mL), and the organic extracts were dried over $MgSO_4$. Pure cis-1,2-diols were obtained by flash chromatography on silica gel (230-400 mesh) and were characterized by IR, MS and NMR spectroscopies. Following a series of control experiments, 20 mol % of $H_2SO_4$ gave the maximum yield; further increase of $H_2SO_4$ did not improve the yield. Using $NaIO_4$ as oxidant was shown the best among hypochlorate, hydrogen peroxide and tert-butyl hydroperoxide.

Using the nano-RuHAP catalyzed protocol, alkenes were selectively converted into corresponding cis-1,2-diol with moderate to good yields (see TABLE 1). α,β-unsaturated alkenes such as ethyl trans-cinnamate, ethyl crotonate, dimethyl fumarate, dimethyl maleate and isophorone can be transformed to their corresponding cis-1,2-diols in 70, 65, 53, 50 and 64% isolated yields, respectively (entries 1-5). Under the Ru-catalyzed conditions, effective oxidations of styrene and 1-dodecene gave styrene glycol (85%) and dodecene glycol (75%) in good yields (entries 6 and 7). Likewise, dihydroxylation of 1,2-disubstituted alkenes including 1,4-diacetoxy-cis-but-2-ene and phenanthrene has been achieved to afford the corresponding cis-1,2-diols in 61 and 60% yields (entries 8 and 9). Using 1-acetoxy cyclohex-2-ene as substrate, the Ru-catalyzed dihydroxylation furnished 1-acetoxy-2,3-dihydroxycyclohexane in 75% yield (entry 10) with the anti-isomer being the major product (anti:syn=9:1). Yet, the catalytic dihydroxylation of trisubstituted alkenes such as (3-benzloxy)-1-methylbut-1-ene appeared to be less effective, and the corresponding cis-1,2-diol was obtained in only 45% yield (entry 11).

The organic products of the catalytic dihydroxylation were identified by their spectral and physical data with the reported data (see: Shing, T. K.-M.; Tai, V. W. F.; Tam, E. K.-M.; Chung, I. H.-F.; Jiang, Q. *Chem. Eur. J.* 1996, 2, 50).

EXAMPLE 2

Recycling refers to the return to an original catalyst so that reaction can begin again. This is particularly important to save the valuable catalyst and minimize product contamination. The nano-RuHAP catalyst was recovered by centrifugation and was used for the second, third and fourth runs under identical reaction conditions. With ethyl trans-cinnamate as substrate, no apparent loss of catalyst activity was observed, and the product cis-1,2-diol was isolated in 80, 82 and 66% yields, respectively. A total product turnover=298 was attained over four consecutive runs. For each cycle of catalyst recovery, ICP-MS analysis of the supernatent solution revealed the residual Ru content was below 5 ppm. It is noteworthy that zero-valent Ru metal powder is completely ineffective catalyst for the dihydroxylation reaction.

Turnover refers to the relative number of molecules of products per number of molecules of catalyst prior to the exhaustion of a given reaction and shows a very important aspect of catalyst efficiency. It should be noted that the turnover number of $RuCl_3$ catalyst do not exceed 168 for methyl trans-cinnamate, a derivative of trans-cinnamate ester (see: Plietker, B.; Niggemann, M. *Org. Lett.* 2003, 5, 3353). The nano-RuHAP-catalyzed protocol is equally effective when operating at a larger-scale. For example, the reaction of ethyl trans-cinnamate (10 mmol) in the presence of nano-RuHAP (0.2 mol %) gave the corresponding cis-1,2-diol in 67% isolated yield (product turnover=330).

EXAMPLE 3

Oxidative Cleavage of Alkenes catalyzed by nano-RuHAP using $NaIO_4$ as Oxidant (see: Yang, D.; Zhang, C. *J. Org. Chem.* 2001, 66, 4814).

The invention relates to a direct method of synthesis of aldehydes and ketones using nano-RuHAP as a general and effective catalyst for the oxidative cleavage of alkenes. To a mixture of 1,2-dichloroethane (5 mL) and distilled water (1 mL) containing alkene (90 mg, 0.5 mmol) and nano-RuHAP (40 mg) was added $NaIO_4$ (214 mg, 1 mmol) by portions over a period of 10 min at room temperature. After complete reaction based on TLC monitoring, excess $NaIO_4$ was quenched by a saturated $Na_2S_2O_3$ solution. The catalyst was separated from the reaction mixture by centrifugation, and the recovered catalyst was washed with water and dried in vacuum before reuses. The supernatant liquid was extracted with $CH_2Cl_2$ (3×10 mL) and the combined organic extracts were dried over anhydrous $Na_2SO_4$. The reaction products were identified and quantified by capillary GC analysis using 1,4-dichlorobenzene as internal standard.

With nano-RuHAP as catalyst, alkenes were cleaved to corresponding aldehydes or ketones in excess yields upon treatment with NaIO₄ (1 mmol) in a 1,2-dichloroethane-H₂O (5:1 v/v) at room temperature for 2-3 hours (TABLE 2). Oxidative cleavage of other stilbene derivatives such as cis-stilbene and 1-methyl-1,2-diphenylethylene under the nano-RuHAP catalyzed conditions produced the carbonyl products in excellent yields (>85%) (entries 2-3). As expected, styrene, α-methylstyrene and trans-β-methylstyrene were found to undergo oxidative cleavage using the "nano-RuHAP+NaIO₄" protocol, and benzaldehyde was obtained in 66-92% yields (entries 4-6). When cyclic aromatic alkenes such as dihydronaphthalene was used as substrate, the corresponding dicarbonyl product was isolated in 86% yield with 76% substrate conversion (entry 7). Likewise, cyclic aliphatic alkenes such as norbornene and cyclooctene were found to undergo effective C=C bond cleavage to afford the corresponding dicarbonyl products in 72-87% yields (entries 8-9).

EXAMPLE 4

Oxidative Cleavage of Alkenes Catalyzed by Nano-RuHAP Using Oxone as Oxidant.

The invention relates to a direct method of synthesis of aldehydes and ketones using nano-RuHAP as a general and effective catalyst for the oxidative cleavage of α,β-unsaturated alkenes. To a mixture of CH₃CN (7.5 mL) and distilled water (5 mL) containing alkene (104 mg, 0.5 mmol) and nano-RuHAP (40 mg) was added a mixture Oxone (770 mg, 1.25 mmol) and NaHCO₃ (330 mg, 2.3 mmol) over a period of 10 min at room temperature. Upon complete reaction based on TLC analysis, excess NaIO₄ was quenched by a saturated Na₂S₂O₃ solution. The catalyst was separated from the reaction mixture by centrifugation, and the recovered catalyst was washed with water and dried in vacuum before reuse. The supernatant liquid was extracted with CH₂Cl₂ (3×10 mL) and the combined organic extracts were dried over anhydrous Na₂SO₄. The reaction products were purified by flash chromatography and were characterized by IR, MS and NMR spectroscopies. "nano-RuHAP+Oxone" protocol would also effect oxidative cleavage of α,β-unsaturated alkenes. When chalcone (0.5 mmol) was treated with Oxone (1.25 mmol) and nano-RuHAP (4 mol %) in a NaHCO₃ buffered MeCN—H₂O (1.5:1 v/v) at room temperature for 3 h, benzaldehyde and benzoic acid were produced (entry 1). Similar oxidative cleavage products were found in isophorone and (+)-pulegone (entry 2,3). Notably, facile oxidative cleavage of C≡C bonds was also observed. For example, subjecting alkynes such as 1-phenyl-1-propyne to the Ru-catalyzed conditions produced benzoic acid in 82% yield (entry 4).

TABLE 1

Nano-RuHAP Catalyzed cis-Dihydroxylation of Alkenes[a]

| entry | alkene | product | yield (%)[b] |
|---|---|---|---|
| 1 | Ph-CH=CH-CO₂Et | Ph-CH(OH)-CH(OH)-CO₂Et | 70 |
| 2 | CH₃-CH=CH-CO₂Et | CH₃-CH(OH)-CH(OH)-CO₂Et | 65 |
| 3 | MeO₂C-CH=CH-CO₂Me (trans) | MeO₂C-CH(OH)-CH(OH)-CO₂Me | 53 |
| 4[c] | MeO₂C-CH=CH-CO₂Me (cis) | MeO₂C-CH(OH)-CH(OH)-CO₂Me | 50 |
| 5 | isophorone | isophorone diol | 64 |
| 6 | long-chain alkene | long-chain diol | 75 |

TABLE 1-continued

Nano-RuHAP Catalyzed cis-Dihydroxylation of Alkenes[a]

| entry | alkene | product | yield (%)[b] |
|---|---|---|---|
| 7 |  |  | 85 |
| 8 |  |  | 61 |
| 9[d] |  |  | 60 |
| 10 |  |  | 75 (anti:syn = 9:1) |
| 11 |  |  | 45 |

[a]Reaction conditions: alkene (2 mmol), nano-RuHAP (40 mg), NaIO$_4$ (1.5 equiv) and H$_2$SO$_4$ (20 mol %) in EtOAc-MeCN—H$_2$O (3:3:1 v/v) at 0° C., reaction time = 30 min.
[b]Isolated yield.
[c]Reaction time = 10 min.
[d]Reaction time = 40 min.

TABLE 2

Nano-RuHAP Catalyzed Oxidative Cleavage of Alkenes[a]

| entry | alkene | time(h) | product | yield (%) |
|---|---|---|---|---|
| 1 |  | 2 | PhCHO | 81[b] |
| 2 |  | 2 | PhCHO | 85[b] |
| 3 |  | 3 | PhCHO<br>PhCOMe | 85<br>89 |
| 4 |  | 2 | PhCHO | 66 |
| 5 |  | 3 | PhCOMe | 92 |
| 6 |  | 3 | PhCHO | 90 |
| 7[d] |  | 3 |  | 86[c] |

TABLE 2-continued

Nano-RuHAP Catalyzed Oxidative Cleavage of Alkenes[a]

| entry | alkene | time(h) | product | yield (%) |
|---|---|---|---|---|
| 8 | (norbornene) | 3 | OHC-cyclopentane-CHO (cis) | 72[c] |
| 9 | (cyclooctene) | 3 | OHC-(CH₂)₆-CHO | 87[c] |

[a]Reaction conditions: alkene (0.5 mmol), nano-RuHAP (40 mg), NaIO₄ (1 mmol), in ClCH₂CH₂Cl—H₂O (5:1 v/v) at room temperature, and the products were identified and qunatified by GC analysis.
[b]Percentage yield was calculated based on 2 equiv of benzaldehyde formed.
[c]Isolated yield.
[d]76% conversion.

TABLE 3

Nano-RuHAP Catalyzed Oxidative Cleavage of α,β-Unsaturated Alkenes[a]

| entry | alkene | time(h) | product | yield (%)[b] |
|---|---|---|---|---|
| 1 | Ph-CH=CH-C(O)-Ph | 4 | PhCHO<br>PhCO₂H | 67<br>72 |
| 2 | (isophorone) | 7 | CH₃C(O)CH₂C(CH₃)₂CH₂CO₂H | 85 |
| 3 | (pulegone-type) | 3 | HO₂C-CH₂CH₂-C*H(CO₂H)- | 84 |
| 4[c] | Ph—≡—CH₃ | 2 | PhCO₂H | 82 |

[a]Reaction conditions: alkene (0.5 mmol), nano-RuHAP (40 mg), Oxone (2.5 equiv) and NaHCO₃ (7.7 equiv) in MeCN—H₂O 1.5:1 at rt.
[b]Isolated yield.
[c]Oxone (4 equiv) and NaHCO₃ (12 equiv).

What is claimed is:

1. A method for synthesizing a cis-1,2-diol from an alkene comprising the step of reacting an oxidant and an acid with the alkene in the presence of a catalytic amount of a solid supported ruthenium nanoparticles as catalyst.

2. The method for synthesizing a cis-1,2-diol from an alkene, an oxidant, and an acid described in claim 1, wherein the alkene has the structure $R_1R_2C=CR_3R_4$, and
where $R_1$ to $R_4$ can be H, alkyl, CN, COOH, COO-alkyl, COO-aryl, CO-alkyl, CO-aryl, O-alkyl, O-aryl, O—CO-alkyl, O—CO-aryl, OCOO-alkyl, OCOO-aryl, N-alkyl₂, N-aryl₂, NH-alkyl, NH-aryl, NO, NO₂, NOH, aryl, fluoro, chloro, iodo, CHO, SO₃H, SO₃-alkyl, SO₂-alkyl, SO-alkyl, CF₃, alkyl is a 1 to 18 carbon-atom hydrocarbon, aryl is an aromatic ring.

3. A method for synthesizing a cis-1,2-diol from an alkene, an oxidant, and an acid as set forth in claim 1, wherein the oxidant includes a hypervalent iodine compound, a hypervalent chlorine compound, hydrogen peroxide or a derivative thereof, a peracid compound, or a derivative thereof.

4. A method for synthesizing a cis-1,2-diol from an alkene, an oxidant, and an acid as set forth in claim 1, wherein the reaction takes place in a solvent and the solvent is a mixture of water and an organic solvent that includes acetonitrile, ethyl acetate, dichloromethane, chloroform, 1,2-dichloroethane, hexane, benzene, toluene, methanol, ethanol, isopropanol, tert-butanol, or mixtures thereof.

5. A method for synthesizing a cis-1,2-diol from an alkene, an oxidant, and acid as set forth in claim 1, wherein the reaction takes place at a temperature between −78 to 40° C.

6. A method for synthesizing a cis-1,2-diol from an alkene, an oxidant, and an acid as set forth in claim 1, wherein the acid include sulfuric acid, nitric acid, hydrochloric acid, and acetic acid.

7. A method for synthesizing a cis-1,2-diol from an alkene and an oxidant and acid as set forth in claim 1, wherein the ruthenium nanoparticles range in size from 1 to 100 nm, and are supported on hydroxyapatite.

* * * * *